United States Patent [19]
Liu et al.

[11] Patent Number: 5,120,422
[45] Date of Patent: Jun. 9, 1992

[54] SODIUM ION SENSOR

[75] Inventors: Meilin Liu; Ashok V. Joshi, both of Salt Lake City, Utah

[73] Assignee: Ceramatec, Inc., Salt Lake City, Utah

[21] Appl. No.: 663,423

[22] Filed: Mar. 1, 1991

[51] Int. Cl.$^5$ .......................................... G01N 27/26
[52] U.S. Cl. ......................... 204/416; 204/153.15; 204/421; 204/422; 204/419
[58] Field of Search ............... 204/421, 422, 424, 414, 204/415, 418, 419, 416, 153.15

[56] References Cited

U.S. PATENT DOCUMENTS

| | | | |
|---|---|---|---|
| 4,085,023 | 4/1978 | Fray | 204/422 |
| 4,182,667 | 1/1980 | Dobson et al. | 204/419 |
| 4,377,460 | 3/1983 | Hirayama et al. | 204/428 |
| 4,645,571 | 2/1987 | Dubreuil et al. | 204/422 |
| 4,759,828 | 7/1988 | Young et al. | 204/415 |
| 4,814,062 | 3/1989 | Redey et al. | 204/422 |
| 4,816,130 | 3/1989 | Karakelle et al. | 204/418 |
| 4,925,544 | 5/1990 | Goldring | 204/414 |
| 4,948,490 | 8/1990 | Venkatasetty et al. | 204/421 |

Primary Examiner—John Niebling
Assistant Examiner—Bruce F. Bell
Attorney, Agent, or Firm—Trask, Britt & Rossa

[57] ABSTRACT

A sodium ion sensor having a composite electrolyte is disclosed. The sodium ion sensor has an outer electrolyte which is insensitive to water and has a high transport activity for sodium ions and an inner electrolyte which is a thin membrane having a very high sodium ion selectivity. The sodium ion sensor having such an electrolyte is sensitive only to the transport of sodium ions and may be operated in aqueous solutions without buffering and in the presence of other alkali ions and alkaline earth metal ions. Sensors of this type operate in EMF mode to give a substantially instantaneous determination of the sodium ion concentration of the aqueous medium being analyzed. The sensor may be used as an on-line sensor directly exposed to the medium to be analyzed.

15 Claims, 4 Drawing Sheets

SODIUM ION SENSOR

BACKGROUND OF THE INVENTION

1. Field

The instant invention relates to electrolytic-type sodium ion sensors which employ a sodium transport electrolyte in conjunction with a pair of electrodes, one of which is exposed to the medium to be analyzed, and the other being a reference electrode. Concentration of the sodium ion is determined by the voltage generated by the difference in ion concentrations between the reference material, which has a known sodium ion concentration, and the medium to be analyzed. The voltage is translated into an ion concentration differential according to the Nernst equation.

2. State of the Art

Ion concentrator analyzers have been utilized in industry for some time. A typical sodium ion analyzer, for example, has a solid sodium ion transport electrolyte in contact with a solution of known concentration and a reference electrode sealed so that an outer surface is exposed to the solution to be analyzed. The other electrode makes contact with the solution to complete the circuit. Since the solid sodium ion transport electrolytes, which are water resistant, such as NASiCON, are influenced by protons, that is the hydrogen ion, the solutions must be buffered to a substantially high pH, typically up to pH>9.0 where H+concentration is very low. Also, other alkaline metal and alkaline earth metal ions may influence detected voltage differentials, that is, some of them may be transported to some small degree in the sodium ion transporting electrolyte. The transportability of protons and other alkali and alkaline metal species causes such sodium ion solid electrolyte sensors to give inaccurate indications of sodium ion concentration.

Other sodium ion concentration analyzers employ chemical analysis when very accurate readings are required. The existing solid sodiumion electrolyte analyzers generally do not give the accuracy provided by wet chemical analyzers.

SUMMARY OF INVENTION

The sensors of the instant invention are an improvement upon existing electrolytic-type sodium analyzers inasmuch as dual or composite electrolytes are utilized. An outer electrolytic membrane is exposed to the solution to be analyzed and is a water-resistant electrolyte such as NASiCON. On the interior of the sensor is a second electrolyte membrane which is specific to sodium ions, i.e. it does not transport protons or other alkali metal or alkaline earth metal ions. This inner membrane is in intimate and contiguous contact with the outer membrane and is in contact with a material of known sodium concentration. The inner membrane electrolyte is protected from contact with the solution to be analyzed by the outer electrolyte. Typical sodium ion-specific membranes are adversely affected by sodium ion-containing solutions, such as aqueous solutions which tend to leach sodium from the membranes. The composite nature of the electrolytes of the instant invention avoids such a problem.

The composite electrolyte is sealed to the end of a sensor probe or, in a preferred mode, the probe is formed of a closed-end NASiCON tube with the inner membrane formed on the interior of the tube end. The analyzer preferably operates in an EMF (electromotive force) mode by detecting the voltage potential difference across the composite electrolyte. Because the inner membrane contains mobile ions, e.g. sodium ions, of the type to be detected, the voltage potential difference is due solely to the difference in concentrations of the ion to be detected between the sample and the reference materials That is, an electromotive force is generated across an electrolyte when a difference in concentration is detected between the reference sodium material and the solution to be analyzed. The potential difference is translated into a reading of concentration of sodium ions in the solution to be analyzed via the Nernst equation.

The sodium analyzer of the instant invention may be modified by utilizing other electrolyte media to detect ions other than sodium. A potassium or calcium analyzer may also be made, for example, of an outer electrolyte wherein the predominantly mobile ion is calcium or potassium. NASiCON may be prepared wherein the predominant mobile ion is potassium. An inner membrane which is potassium specific, such as potassium tungstate, may be utilized. Thus, the invention may be modified by utilizing various composite electrolytes to a measure specific alkali metal ion or alkaline earth metal ion. The most common ion to be detected and one having frequent widespread significance, especially in aqueous media, is the sodium ion.

BRIEF DESCRIPTION OF THE INVENTION

The instant invention relates to a sodium ion detector or detector for another alkali metal ion or alkaline earth metal ion, utilizing a composite, ion-conducting membrane (composite electrolyte) to determine the concentration difference between the sodium ion concentration in a standard material and the sodium ion concentration in a solution to be analyzed such as an aqueous solution. The sodium ion sensor of the instant invention measures the potential difference (electromotive force, identified herein as EMF) between the sodium ion concentration in the standard and the sodium ion concentration in the liquid material to be analyzed.

While sodium ion sensors are generally known, the uniqueness of the instant invention resides particularly in the composite electrolyte used as a sodium ion conductor and its utilization in a unique manner in a sensor.

Figure 1:
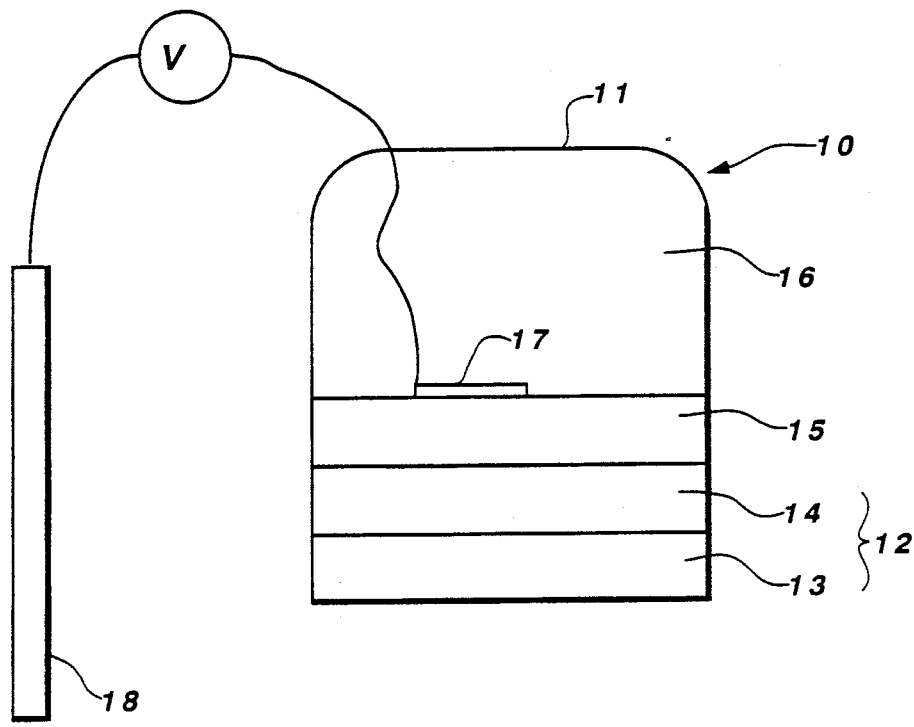
FIG 1 is a schematic view of the sensor of the instant invention illustrating a composite electrolyte.

Further description of the invention may be facilitated by reference to the attached drawings. FIG. 1 is a schematic view of the sensor of the instant invention illustrating a composite electrolyte. The sensor 10 has a shell 11 which is an enclosure with an open end in which the composite electrolyte 12 is sealed. Composite electrolyte 12 has an outer membrane 13 and an inner membrane 14 and in the illustration of FIG. 1, the top surface of the inner membrane 14 is in contact with a film of sodium metal 15. Inasmuch as sodium metal is very reactive with oxygen and water the chamber 16 above the sodium metal is preferably filled with a dry inert gas such as nitrogen. An inner electrode 17 is attached to the top surface of the sodium metal 15.

The sodium metal 15 can be alternatively replaced by a sodium-containing compound (such as $NaWO_3$) or sodium alloy as reference material to fix the sodium activity at the inner electrode.

A sample electrode 18 is connected electrically through a voltmeter to the inner electrode 17. The inner electrode 17 has a fixed potential since it is attached to a material 15 which has a fixed sodium activity. Thus, the voltmeter will indicate the electromotive force generated across the composite electrolyte 12 when the sample electrode and the composite electrolyte are in contact with a solution containing sodium ions. The inner electrode 17 may be silver while the sample electrode may be a silver or silver/silver chloride electrode.

The composite electrolyte 12 consists of an outer membrane which is a solid, impervious material containing mobile ions of the type to be detected. Other species of ions, which may also be mobile, may be frequently present in the outer membrane, usually in very minor quantities. Materials useful in the outer membrane 13 are sodium-containing glasses, certain sodium-containing ceramics generally known as NASiCON, beta alumina, sodium ion conducting glasses generally known as Nasiglass and the like. The material used in the outer membrane 13 must be chemically stable and insoluble in the material to be analyzed. For example, if the material to be analyzed is an aqueous solution containing sodium ions then the outer membrane must not be leached or dissolved by water or other such solvent-containing sodium ions. In general, NASiCON is more water resistant than sodium beta alumina, although sodium beta alumina may be used effectively with non-aqueous solutions wherein the solvent does not leach sodium from the beta alumina. Generally, glass and ceramic outer membranes are preferred.

Figure 2:
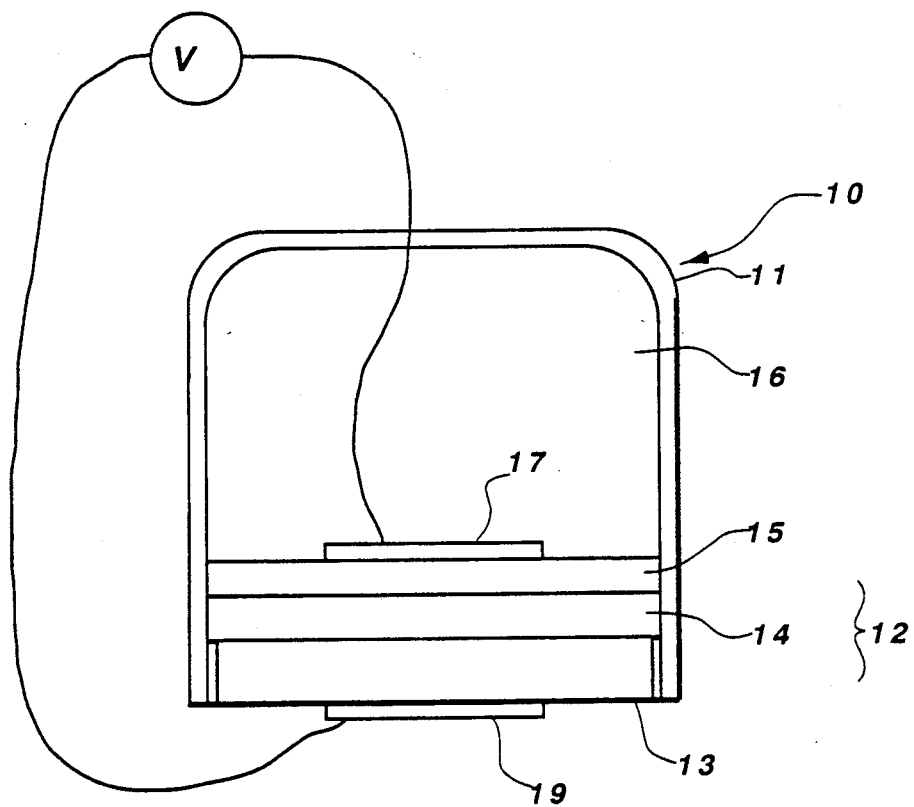
FIG. 2 is a schematic view of a sensor of the instant invention illustrating a composite electrolyte with the sample electrode attached to the outer surface of the electrolyte.

Another version of the sensor (analyzer) is illustrated in FIG. 2 wherein the sensor 10 is an integrated structure wherein the electrodes are both part of the probe. The sensor involves a probe shell 11 with a composite electrolyte 12 composed of an outer membrane 13, an inner membrane 14 and a sodium standard material 15, e.g. sodium metal or a solid sodium salt. The space 16 above the sodium standard material is filled with a dry, inert gas if the inner membrane or the sodium standard material is air or moisture sensitive.

An inner electrode 17 is attached through a voltmeter to a sample electrode 19 (porous) which is attached to the external surface of the composite electrode. Generally, electrode 19 does not cover the total external surface of the electrolyte 13. If electrode 19 does cover the entire external surface of electrolyte 13, then electrode 19 must be porous to permit sodium ion transport through the electrode 19 so that the material, for example, a dilute sodium ion-containing material such as an aqueous solution containing sodium salts, for example, beer, can be analyzed.

Although the invention is generally described with reference to sodium ions wherein the outer membrane contains mobile sodium ions, sensors may be developed wherein the mobile ion is a proton or an ion of potassium, calcium, proton, or some other alkali metal or alkaline earth metal, including other metals which may be formulated in a NASiCON or beta alumina structure such as lead, silver, and the like.

For purposes of this invention, preferred outer membranes include NASiCON, which generally has the following formula:

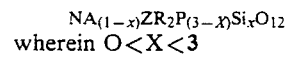

wherein $0 < X < 3$ which, in preferred form is $Na_3Zr_2PSi_2O_{12}$ Glasses containing a relatively mobile ion may be utilized as the outer membrane. Soda glasses, particularly glasses wherein the sodium ion is relatively mobile, includes those sodium glasses which have been used as electrolytes in environments such as the sodium-sulfur battery. Sodium silicates such s $Na_2O-ZrO_2-Al_2O_3-SiO_2$ and sodium borate are further examples of useful outer membrane materials.

These materials may be readily formed into closed end tubes or into thin, impervious discs and readily sealed into the end of the shell or enclosure 11 of a typical sodium sensor probe of the instant invention. It is important that the disc be impervious so that water does not pass through the outer membrane 13 to come in contact with the inner membrane 14. The inner membrane 14 must be protected from contact with the aqueous environment inasmuch as the inner membrane would be readily leached and the sensor would have a short-lived effectiveness.

The outer membrane which is generally a solid, rigid impervious member such as a ceramic disc made of NASiCON, is sealed into the outer shell of the sensor probe by a low melting glass or by a resinous material which is aqueous resistant (insoluble in water) and which contains no mobile ions so that no "short circuiting" of the outer membrane is possible.

The inner membrane 14 is preferably formed in place on the inner surface of the outer membrane 13 so that an intimate physical bond exists between the outer and inner membrane. One useful technique is to use a polymer-based electrolyte such as a polyethylene oxide polymer doped with $NaClO_4$ having a high molecular weight dissolved in solvent such as acetonitrile A soluble sodium salt such as sodium triflate can be dissolved in the solution in place of or in addition to other sodium salts. The solution is cast in place on top of the outer membrane, that is, on the internal surface of the outer membrane, and the solvent is permitted to evaporate to leave a thin, solid film having a thickness of about 10 to about 20 microns. An inner membrane formed in this manner is physically bonded to the internal surface of the outer membrane and an electrically conductive surface exists between the membranes. Intimate contact between the two membranes is essential to ensure an electrical circuit whereby sodium ions, for example, can travel through both membranes.

Another technique for forming the inner membrane is to swell an appropriate polymer, such as polyethylene oxide, with a solvent such as acetonitrile, which contains dissolved sodium salts such as sodium chlorate, sodium sulfate, sodium carbonate, sodium triflate, so that the sodium salt becomes distributed throughout the whole body of the polymer, then pressing the swollen polymer against the internal surface of the outer membrane and maintaining sufficient pressure during the evaporation of the solvent so that a strong physical bond is formed between the inner surface of the outer membrane and the filmy inner membrane. Alternatively, the inner layer could be a thin film of an inorganic sodium salt such as $Na_2SO_4$, $Na_2WO_3$, $Na_2CO_3$, NaI, and the like.

The inner membrane is not required to be very thick, however, it is preferably be completely continuous so that the whole inner surface of the outer membrane is covered. Preferably, the inner membrane has a substantially uniform thickness and is substantially pore free. Bonding between the inner surface of the outer membrane and the inner membrane may be enhanced by having a slightly roughened or porous internal surface on the outer membrane However, the outer membrane must also not contain pores which penetrate its thickness.

A further method of bonding the inner membrane to the outer membrane is by forming a solution or swollen polymer which is then doped with an appropriate sodium salt, and evaporating the solvent until a film of polymer doped with a sodium salt is formed. The polymer may then be pressed against the inner surface of the outer membrane and heated until the softening point of the polymeric membrane is exceeded so that an intimate physical bond is formed between the two membranes. Since the outer membrane is generally a ceramic or a high-temperature melting glass, the outer membrane will not be adversely affected by the temperature to which the composite electrolyte is heated in order to exceed the softening point of the polymeric membrane.

The outer membrane generally has a thickness of about 0.1 to about 3.0 mm with a typical diameter of about one-fourth to about one-half inch. Membranes with greater thickness may readily be used if desired. A ceramic membrane such as NASiCON or beta alumina is generally sintered to a density of about 96% or more of theoretical density, that is, a very low pore content, so that the membrane is not permeated by water molecules.

Sodium metal can be put in place in a molten condition by placing the whole sensing element in an inert atmosphere while the sodium is being heated. An appropriate electrode is then attached to the sodium metal and interconnected by a voltmeter to an external electrode which may be immersed in the same solution as the NASiCON membrane. Sodium metal can also be precipitated inside the tube by electrowinning of a sodium salt. A solid sodium salt or alloy may also be utilized in place of sodium metal. A suitable inner electrode may be formed from silver, platinum and other noble metals. The electrode must be intimately bonded to the inner membrane.

Sensors made in accordance with the instant invention are very accurate and have a rapid response time. Furthermore, such sensors can be used on-line to provide continuous monitoring of a sodium ion- (or other mobile ion) containing solution.

The sensor of this invention can detect sodium concentrations as low as 1 ppm, with an accuracy of about 95%. Such accuracy is attainable without buffering or other treatment of the ion-containing solution.

Beer, for example, is regularly monitored for sodium content. The sodium specifications for beer are rather exacting and an accurate, on-line system for constantly monitoring beer production is especially desirable.

Figure 3:
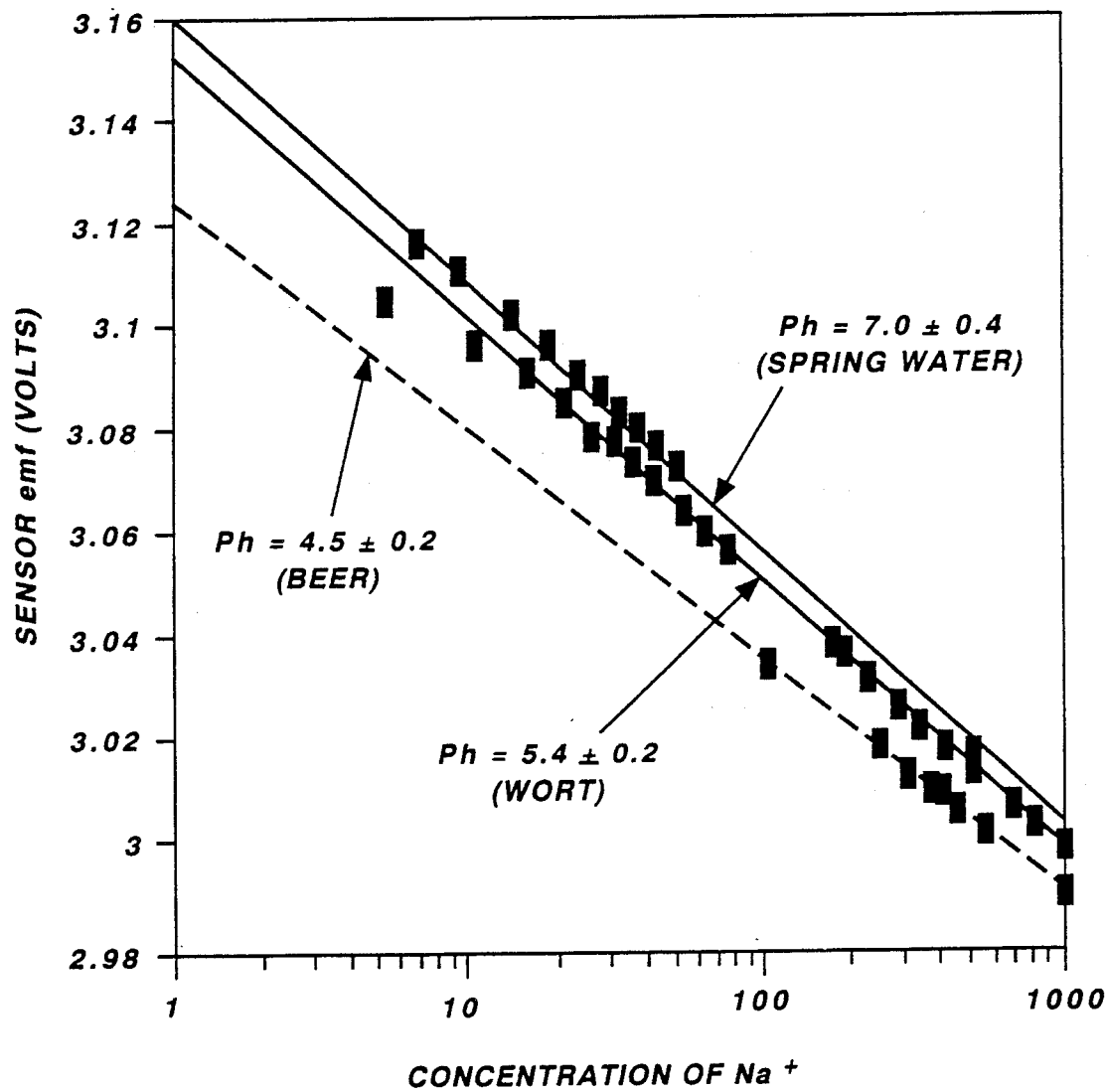
FIG. 3 is a graph of a calibration curve comparing the concentration of sodium ions to sensor and in volts for various liquids of varying pH.

In FIG. 3, a concentration of sodium ions is calibrated for the sensor EMF.

Figure 4:
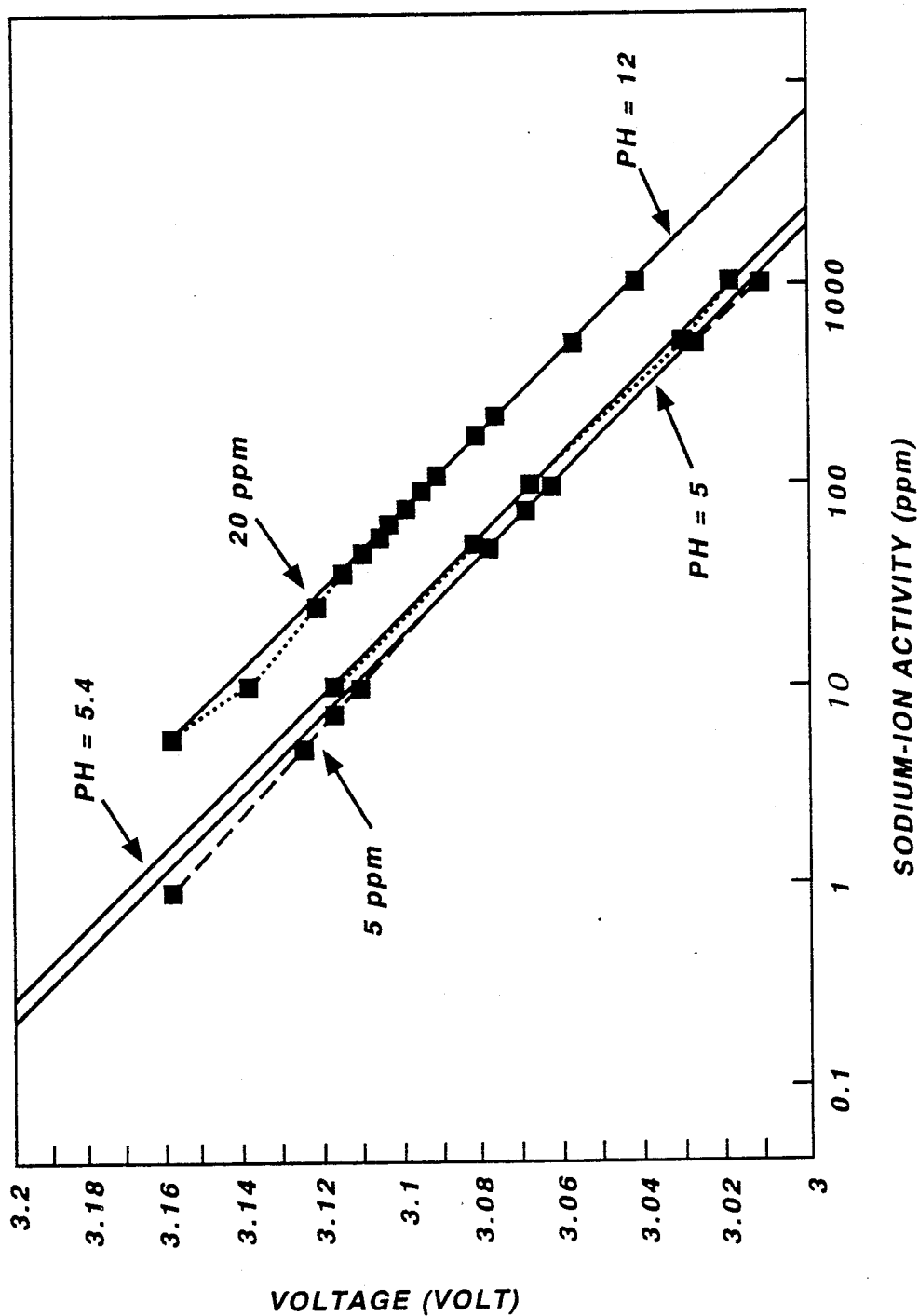
FIG. 4 is a graph of a sodium ion activity set forth in parts per million compared to voltage, for example, under varying pH conditions.

In FIG. 4, a plot is made of voltage vs. sodium ion in parts per million for aqueous salt solutions having various pH.

Once calibration has been accomplished for a given solution or process, then direct measurement of ion concentration can be directly determined from an analyzer employing the unique sensors of the instant invention.

Figure 5:
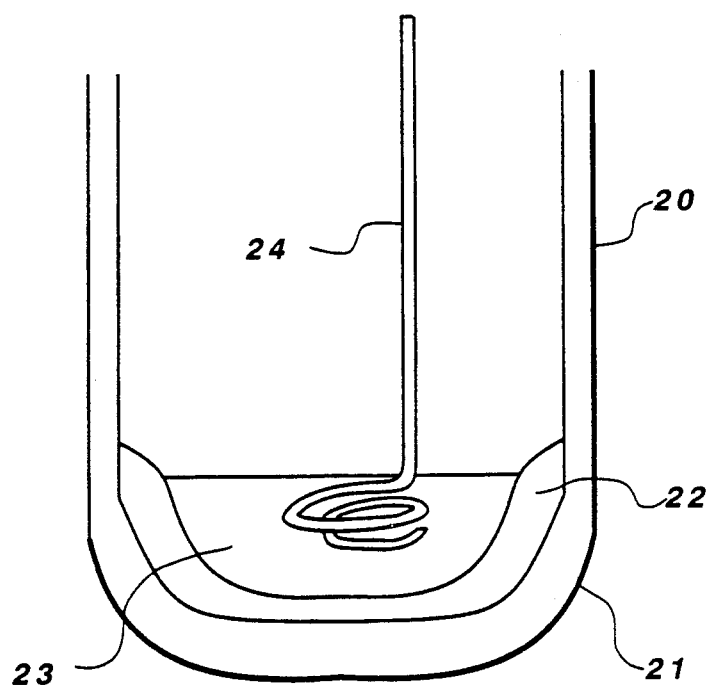
FIG. 5 is a cross-sectional view of a ceramic electrolyte tube with an inner cation-selective membrane and a standard cation material of a known cation concentration.

An example of a sodium sensor constructed in accordance with the instant invention utilizing a tubular shell 20 is illustrated in FIG. 5. The shell is constructed of an electronically insulating, ionically conductive, corrosion-resistant material such as NASiCON The tube 20 has an internal diameter generally of less than about 25 mm, typically being about 5 to 10 mm. The shell has a length of at least about 2.5 mm, although various lengths may be employed. The length of the tube may be as long as 100 mm so that it is sufficient to provide a handle to hold to insert the sensor end of the tube into a material to be analyzed.

Alternatively, the shell may be constructed of metal, e.g., stainless steel, with an insulating material, e.g., a sealing glass used to hold the sensing elements in the shell and to provide electrical isolation between the shell and the sensing elements. If a metal shell is utilized, the open end of the tube is used to contain a NASiCON disk sealed to form a liquid-tight enclosure in the manner illustrated in FIGS. 1 and 2.

The NASiCON tube 20 has a wall thickness of about 0.5 to about 1.5 mm, with a thickness of about 1.0 mm being typical. The closed end 21 of the tube forms an outer sodium sensing element. An inner film 22 which transports only sodium ions is formed from sodium sulfate, sodium tungstate or a similar sodium-containing material in which the sodium ion is mobile. Such materials include sodium salts wherein the sodium is ionically bonded.

A film 22 of $Na_2SO_4$ is formed on the interior of the closed end of the NASiCON tube by placing a small quantity of $Na_2SO_4$ particles in the tube and then heating the closed end of the tube to a temperature greater than the melting point of $Na_2SO_4$, approximately 800° C., to melt the $Na_2SO_4$. Because of the thinness of the $Na_2SO_4$ film, its wetting of the NASiCON tube and capillary action, a "U"-shaped film about 0.1 mm thick is formed on the inside of the closed end of the tube. During melting of the $Na_2SO_4$, the tube may be tilted and rotated to enhance the formation of such a "U"-shaped $Na_2SO_4$ film ($Na_2SO_4$ "well"). An inner electrode 23 is formed by placing a powdery mixture of sodium tungstate and silver into the $Na_2SO_4$ "well" and heating the mixture to melt it, then allow it to cool to form an inner electrode. An electrode lead 24 may be inert in the powdery mixture to form an intimate contact between the lead and the electrode when the powder is melted and cooled.

Sodium salts useful as a standard sodium ion-containing material of known sodium ion concentration include sodium sulfate, sodium tungstate and other sodium salts which can be formed into a solid integral, structural film on the inside of the outer sodium membrane, which, for the purposes of this invention, is a glass or ceramic, and is preferably a water-resistant ceramic such as NASiCON. Preferred sodium salts are those which wet the outer membrane when they are in a molten condition The silver and sodium tungstate mixture has a melting point of about 690° C., which is less than that of $Na_2SO_4$. Thus, by careful heating to a temperature less than about 750° C., only the silver-sodium tungstate mixture is melted. The electrode lead 24 may be made of silver, for example, which has a melting point of about 961° C.

While the sodium ion sensors of this invention may be constructed to have high temperature characteristics, for example, useful in measuring the sodium ion concentration in liquids at temperatures up to 500° C., or even higher, significant utility exists for low temperature measurements, for example, in aqueous systems at temperatures below about 200° C. Thus, the materials used in the instant sensors should be temperature resistant at temperatures of at least 500° C., or even higher. Furthermore, the manner of constructing the sensors may dictate that each component of the sensor have high temperature resistance.

It is important that the sodium salts used as a sodium ion-containing material be free of other alkali metal or alkaline earth metal ions and that the only cations present are sodium ions. Furthermore, the sodium salts must make excellent contact with the NASiCON, or other outer membrane. One technique for ensuring each contact is to melt the sodium salt and pour it into a NASiCON or glass tube, for example, then allow the sodium salt to cool to a solid, crystalline film Such a film must have sufficient structural integrity to withstand application of an electrode, e.g., applied by sputtering or as a molten mass.

While the invention has been described particularly as a sodium ion sensor, in its broader aspects the invention is useful as a selective cation sensor for determining the concentration of a particular cation species in a liquid medium, which may include molted media A cation sensor, in accordance with this invention, has a sensor probe for inserting in said liquid media, a reference electrode which may be attached to the outer portion of the probe and a millivoltmeter interconnected between said reference electrode and an electrode containing within said probe and isolated from said liquid media.

The probe, in a preferred mode has an enclosure constructed of a material which is chemically and electronically inert to said liquid media. The enclosure may be constructed of a cationically conductive ceramic or glass closed end tube wherein said conductive ceramic or glass contains a predetermined mobile cation in predominance among mobile cations present. The closed end of the ceramic or glass tube acts as a cationically conductive outer membrane. On the inside of the closed end of the tube is an inner membrane formed of a material which contains mobile cations only of the cation species in predominance in said outer membrane. If other cation species are present in said inner membrane, they are present in such insignificant numbers as to have no effect on any measuring capabilities for a sensor using the instant probe. The inner membrane is in intimate contact with the outer membrane.

As standard cation material of a particular cation species of known concentration is in intimate contact with the inner membrane. The sodium salt mixtures used as a standard cation material are exemplary materials. A calcium ion detector utilizing a calcium beta-alumina electrolyte and a calcium sulfate inner membrane may utilize a calcium salt mixture, e.g. a mixture of calcium tungstate and silver, as a standard calcium ion material of a known calcium ion concentration.

It is possible to use the same sodium, or other cation, salt in the ion-selective interior membrane as in the standard sodium, or other cation, material provided that the standard cation material is detected with another material so that the sodium, or other cation, concentration will be different in the standard material than in the membrane Electronically conductive metals are good diluents inasmuch as they improve the electronic conductivity of the standard material as well as charge the sodium ion (or other cation) concentration per unit volume.

Advantages of the instant sensor reside in its simplicity of construction, its use in situ to give immediate, accurate detection of sodium ion concentration, and its durability in various kinds of media, its high temperature resistance and its inertness to the presence of protons and other cations.

What is claimed:

1. A sodium ion sensor for selectively sensing sodium ions in the presence of other ions and varying pH conditions comprising:
   an inner electrode;
   a standard sodium ion material of a known sodium ion concentration, said standard material being in intimate contact with said inner electrode;
   solid electrolyte comprising:
      a first outer membrane adapted to contact a sodium ion solution to be analyzed, said outer membrane being insoluble in said sodium ion solution to be analyzed and being a sodium ion conductor, and
      a second membrane in intimate contact with said standard sodium ion material and with said outer membrane and containing substantially only sodium ions as mobile, conductive ions;
   a reference electrode in contact with said sodium ion solution to be analyzed and electrically connected through a voltmeter to said inner electrode, said voltmeter sized to detect the EMF generated across said composite electrolyte.

2. The sodium ion of claim 1 wherein said standard sodium ion material is a solid material selected from the class of metallic sodium and sodium-containing compounds.

3. The sodium ion sensor of claim 1 wherein said outer membrane is an impervious ceramic or glass containing a mobile sodium ion.

4. The sodium ion sensor of claim 1 wherein said inner membrane is a polymeric material containing sodium ions.

5. The sodium ion sensor of claim 4 wherein said polymeric material contains a sodium salt.

6. The sodium ion sensor of claim 4 wherein said inner membrane is physically bonded to said outer membrane.

7. The sodium ion sensor of claim 4 wherein said polymeric material is a high molecular weight polyethylene oxide.

8. The sodium ion sensor of claim 1 wherein said inner membrane is a sodium salt with high sodium ion selectivity.

9. The sodium ion sensor of claim 8 wherein said sodium salt is electronically conductive.

10. The sodium ion sensor of claim 3 wherein said ceramic is NASiCON, beta-alumina, or Nasiglass.

11. The sodium ion sensor of claim 10, wherein said ceramic is NASiCON.

12. A sodium ion sensor selectively sensing sodium ions in the presence of other ions and under varying pH conditions, comprising:
- a reference electrode/electrolyte system, said electrolyte containing a predetermined concentration of sodium ions; and
- a dual solid electrolyte having an outer sodium-transporting membrane adapted to be in contact with the liquid to be analyzed, and an inner sodium ion-transporting electrolyte exposed to the interior surface of said outer membrane.

13. The sodium ion sensor of claim 1 wherein said standard sodium ion material of a known sodium ion concentration is a sodium-containing compound.

14. The sodium ion sensor of claim 13 wherein said sodium-containing compound is a compound selected from the class consisting of sodium alloys, sodium metal, and sodium salts.

15. A cation sensor probe for use in a sensor determining the concentration in a liquid medium of a particular cation species, comprising:
- an inner electrode;
- a standard cation material of a known cation concentration of the cation species to be analyzed, said standard cation material being in intimate contact with said inner electrode;
- a dual solid electrolyte having an outer membrane which contains mobile cations of the species to be detected, said outer membrane being inert to said liquid medium and an inner membrane in intimate contact with said standard cation material and with said outer membrane and a predetermined cation as substantially the only mobile, conductive cations in said inner membrane; and
- an enclosure means for enclosing said inner electrode, standard cation material and dual electrolyte whereby only the outer surface of said outer membrane is exposed to said liquid medium.

* * * * *